United States Patent
Oishi et al.

(10) Patent No.: US 11,186,952 B2
(45) Date of Patent: Nov. 30, 2021

(54) COMPOSITION WHICH CONTAINS COMPOSITE FIBERS COMPOSED OF INORGANIC PARTICLES AND FIBERS

(71) Applicant: NIPPON PAPER INDUSTRIES CO., LTD., Tokyo (JP)

(72) Inventors: Masatoshi Oishi, Tokyo (JP); Naoyuki Sugawara, Tokyo (JP); Shisei Goto, Tokyo (JP)

(73) Assignee: NIPPON PAPER INDUSTRIES CO., LTD., Tokyo (JP)

( * ) Notice: Subject to any disclaimer, the term of this patent is extended or adjusted under 35 U.S.C. 154(b) by 154 days.

(21) Appl. No.: 16/485,755

(22) PCT Filed: Feb. 9, 2018

(86) PCT No.: PCT/JP2018/004685
§ 371 (c)(1),
(2) Date: Aug. 13, 2019

(87) PCT Pub. No.: WO2018/151050
PCT Pub. Date: Aug. 23, 2018

(65) Prior Publication Data
US 2020/0048839 A1  Feb. 13, 2020

(30) Foreign Application Priority Data
Feb. 14, 2017  (JP) .............................. JP2017-025428

(51) Int. Cl.
*D21H 15/10* (2006.01)
*A61L 9/01* (2006.01)
*D21H 11/04* (2006.01)
*D21H 11/20* (2006.01)
*D21H 17/70* (2006.01)
*D21H 21/52* (2006.01)
*D21H 27/00* (2006.01)

(52) U.S. Cl.
CPC ............... *D21H 15/10* (2013.01); *A61L 9/01* (2013.01); *D21H 11/04* (2013.01); *D21H 11/20* (2013.01); *D21H 17/70* (2013.01); *D21H 21/52* (2013.01); *D21H 27/00* (2013.01); *A61L 2209/22* (2013.01)

(58) Field of Classification Search
USPC ........................................................ 162/146
See application file for complete search history.

(56) References Cited

U.S. PATENT DOCUMENTS

| | | | |
|---|---|---|---|
| 5,897,673 A | 4/1999 | Nishida | |
| 5,945,211 A | 8/1999 | Yamaguchi | |
| 5,981,052 A | 11/1999 | Sugiyama | |
| 2003/0176827 A1 | 9/2003 | Chandra | |
| 2005/0038138 A1 | 2/2005 | Hutte | |
| 2005/0257909 A1 | 11/2005 | Lindgren | |
| 2007/0131360 A1 | 6/2007 | Sipila | |
| 2010/0331457 A1 | 12/2010 | Buri | |
| 2017/0107668 A1 | 4/2017 | Fukuoka et al. | |
| 2017/0113945 A1 | 4/2017 | Fukuoka et al. | |

FOREIGN PATENT DOCUMENTS

| | | |
|---|---|---|
| CN | 104549283 | 4/2015 |
| EP | 0 938 925 A | 9/1999 |
| EP | 3 127 868 A | 2/2017 |
| EP | 3127867 | 2/2017 |
| EP | 3 498 674 A | 6/2019 |
| JP | 2-104712 | 4/1990 |
| JP | 3-153767 | 7/1991 |
| JP | 7145315 | 6/1995 |
| JP | 9-241967 | 9/1997 |
| JP | 9-286615 | 11/1997 |
| JP | 10-120923 | 5/1998 |
| JP | 10165489 | 6/1998 |
| JP | 2003 047647 A | 2/2003 |
| JP | 2003342872 | 12/2003 |
| JP | 2007-528947 | 10/2007 |
| JP | 2008-196067 | 8/2008 |
| JP | 2009209498 | 9/2009 |
| JP | 2011-506789 | 3/2011 |
| JP | 2013-010891 | 1/2013 |
| JP | 2013-241713 | 12/2013 |
| JP | 2014-070158 | 4/2014 |
| JP | 2015-071843 | 4/2015 |
| JP | 2015-073419 | 4/2015 |
| JP | 2015-199660 | 11/2015 |
| JP | 2015199658 | 11/2015 |
| JP | 201653238 | 4/2016 |
| JP | 2016-120488 | 7/2016 |
| JP | 2018-038953 | 3/2018 |
| WO | 2010074311 | 7/2010 |
| WO | 2010/095574 | 8/2010 |
| WO | 2015152269 | 10/2015 |
| WO | 2016/031749 | 3/2016 |

OTHER PUBLICATIONS

Office Action for Japanese Patent No. 6403932, dated Jan. 9, 2020.
Notification for Written Argument filed in connection with Opposition No. 2019-700271, dated Sep. 23, 2020 and partial translation (of the portion of the original document outlined by the red border).
EESR for European patent application 18753643.8 dated Dec. 13, 2019.
English Translation of International Preliminary Report on Patentability in PCT/JP2018/004685, dated Aug. 29, 2019.
International Search Report in PCT/JP2018/004685 dated May 1, 2018.
Office Action for JP2018-114540 dated Mar. 12, 2019.

*Primary Examiner* — Mark Halpern
(74) *Attorney, Agent, or Firm* — Kristina Castellano; Castellano PLLC (57) ABSTRACT

A composition in accordance with an aspect of the present invention includes: composite fibers composed of inorganic particles and fibers; and at least one of (i) different-type inorganic particles which are different in type from the inorganic particles, (ii) different-type fibers which are different in type from the fibers, and (iii) organic particles.

10 Claims, 1 Drawing Sheet

COMPOSITION WHICH CONTAINS COMPOSITE FIBERS COMPOSED OF INORGANIC PARTICLES AND FIBERS

CROSS REFERENCE TO RELATED APPLICATION

This is a U.S. National Stage application of PCT/JP2017/004685 filed on Feb. 9, 2018, which claims priority to Japan Patent Application No. 2017-025428 filed on Feb. 14, 2017, the contents of which are hereby incorporated herein by reference.

TECHNICAL FIELD

The present invention relates to a composition which contains composite fibers composed of inorganic particles and fibers.

BACKGROUND ART

Patent Literature 1 discloses a product in which calcium carbonate is utilized as a composite with fibers.

As general deodorizing materials, a fiber product carrying metal ions, and silver-carrying fine cellulose are known (Patent Literatures 2 and 3). Moreover, as flame retardant materials, magnesium carbonate and aluminum hydroxide are known.

CITATION LIST

Patent Literature

[Patent Literature 1]
Japanese Patent Application Publication, Tokukai, No. 2015-73419
[Patent Literature 2]
International Publication No. WO2015/152269
[Patent Literature 3]
Japanese Patent Application Publication, Tokukai, No. 2014-70158

SUMMARY OF INVENTION

Technical Problem

As above described, fibers having various functions are reported, and a fiber product that has further improved functionality is demanded. An aspect of the present invention is accomplished in order to meet such a demand, and an object of the present invention is to provide a fiber product having higher functionality.

Solution to Problem

The present invention encompasses but not limited to the following features:

(1) A composition including: composite fibers composed of inorganic particles and fibers; and at least one of (i) different-type inorganic particles which are different in type from the inorganic particles, (ii) different-type fibers which are different in type from the fibers, and (iii) organic particles.

Advantageous Effects of Invention

According to an aspect of the present invention, it is possible to bring about an effect of providing a fiber product having higher functionality.

DESCRIPTION OF EMBODIMENTS

[Composition]

The composition in accordance with an aspect of the present invention includes: composite fibers composed of inorganic particles and fibers; and at least one of (i) different-type inorganic particles which are different in type from the inorganic particles, (ii) different-type fibers which are different in type from the fibers, and (iii) organic particles. From this, it is possible to provide the unique composition which has characteristics of both the fibers and inorganic particles which constitute the composite fibers and also has functions of different-type fibers and different-type inorganic particles which are contained in the composition and are of types different from the fibers and inorganic particles. For example, by using deodorant composite fibers in combination with fibers carrying metal ions such as gold, copper, or silver and/or an inorganic material such as active carbon or silica which has a large specific surface area, it is possible to enhance deodorizing property. Moreover, depending on types of inorganic particles and fibers, it is possible to improve functions such as fire resistance and radiation shielding property.

[Composite Fibers]

The composite fibers contained in the composition in accordance with an aspect of the present invention are composite fibers composed of inorganic particles and fibers. According to the composite fiber contained in the composition in accordance with an aspect of the present invention, fibers and inorganic particles do not merely mixedly exist but fibers and inorganic particles are bonded together by a hydrogen bond or the like. Therefore, the inorganic particles are less likely to fall off even by the disaggregation process. A strength of the bond between fibers and inorganic particles in the composite fibers can be evaluated, for example, by ash yield (%). For example, in a case where the composite fibers are in a sheet form, the strength of the bond can be evaluated by a numerical value of (ash content of sheet÷ash content of composite fibers before disintegration)×100. Specifically, after disintegration for 5 minutes with a standard disintegrator defined in JIS P 8220-1: 2012 while adjusting a solid concentration to 0.2% by dispersing the composite fibers in water, an ash yield of a sheet obtained by using 150-mesh wires according to JIS P 8222: 1998 can be used for evaluation. In a preferable aspect, the ash yield is not less than 20% by mass and, in a more preferable aspect, the ash yield is not less than 50% by mass. That is, in a case where inorganic particles are made into composite fibers with use of fibers and, for example, the composite fibers are in a sheet form, the inorganic particles are more likely to remain in the composite fibers and it is also possible to obtain the composite fibers in which the inorganic particles are not aggregated but are uniformly dispersed, unlike a case in which inorganic particles are simply mixed with fibers.

The composite fibers are obtained by a method for synthesizing inorganic particles in a solution containing fibers. It is preferable that 15% or more of a surface of each of the fibers in the composite fibers is covered with inorganic particles. In a case where the fiber surface is covered with the inorganic particles with such an area ratio, a characteristic attributable to the inorganic particles is greatly brought about, while a characteristic attributable to the fiber surface becomes small. According to the composite fiber, a coverage (area ratio) of fiber by inorganic particles is more preferably 25% or more, further preferably 40% or more. According to the method, it is possible to suitably produce composite fibers having a coverage of 60% or more, 80% or more. An upper limit of the coverage can be set as appropriate in accordance with the purpose of use and is, for example, 100%, 90%, 80%. In a preferable aspect of the composite fibers obtained by the method, it is clear from a result of electron microscopy that inorganic particles are generated on outer surfaces of fibers.

A content of composite fibers contained in the composition is preferably 10% or more and 100% or less, more preferably 20% or more and 100% or less, with respect to a total weight of the composition.

[Inorganic Particles]

The inorganic particles constituting the composite fibers can be selected as appropriate depending on the purpose of use of the composition, and are preferably water-insoluble or poorly water soluble inorganic particles. The inorganic particles are preferably insoluble or poorly soluble in water, because the inorganic particles may be synthesized in a water system and the composite fibers may be used in a water system.

The inorganic particles refer to a simple metal or a metal compound. The metal compound is so-called inorganic salt that is obtained by an ionic bond of positive ions of metal (e.g., $Na^+$, $Ca^{2+}$, $Mg^{2+}$, $Al^{3+}$, $Ba^{2+}$, or the like) and negative ions (e.g., $O^{2-}$, $OH^-$, $CO_3^{2-}$, $PO_4^{3-}$, $SO_4^{2-}$, $NO_3^-$, $Si_2O_3^{2-}$, $SiO_3^{2-}$, $Cl^-$, $F^-$, $S^{2-}$, or the like).

Specific examples of the inorganic particles include a compound containing at least one metal selected from the group consisting of gold, silver, titanium, copper, platinum, iron, zinc, and aluminum. The inorganic particles can also be calcium carbonate (light calcium carbonate, heavy calcium carbonate), magnesium carbonate, barium carbonate, aluminum hydroxide, calcium hydroxide, barium sulfate, magnesium hydroxide, zinc hydroxide, calcium phosphate, zinc oxide, zinc stearate, titanium dioxide, silica composed of sodium silicate and mineral acid (white carbon, silica/calcium carbonate composite fibers, silica/titanium dioxide composite fibers), calcium sulfate, zeolite, hydrotalcite, and the like. As the calcium carbonate-silica complex, in addition to the complexes of calcium carbonate and/or light calcium carbonate and silica, amorphous silica such as white carbon can be used in combination. The above exemplified inorganic particles can be used alone or two or more types of those inorganic particles can be used in combination, provided that those inorganic particles do not disturb synthetic reactions in the solution containing fibers. For example, in a case where the composite fibers are made to have a deodorizing function or opacity, it is more preferable to employ a compound containing at least one metal selected from the group consisting of gold, silver, titanium, copper, platinum, iron, zinc, and aluminum. In a case where the composite fibers are made to have a function of flame retardancy, it is preferable to employ calcium carbonate, magnesium carbonate, aluminum hydroxide, barium sulfate, hydrotalcite, magnesium hydroxide, calcium carbonate, calcium phosphate, or silica, and it is particularly preferable to employ calcium carbonate, magnesium carbonate, aluminum hydroxide, barium sulfate, or hydrotalcite. In a case where the inorganic particles in the composite fibers are hydrotalcite, it is more preferable that the ash of composite fibers of hydrotalcite and fibers contains at least one of magnesium and zinc in an amount of not less than 10% by weight. Note that the "compound containing a metal" can be a simple metal or can be a compound containing metal ions. That is, the inorganic particles can be particles of a simple metal or can be particles of a compound containing metal ions.

A synthetic method of the inorganic particles can be either a gas-liquid method or a liquid-liquid method. An example of the gas-liquid method is a carbon dioxide process in which, for example, magnesium carbonate can be synthesized by reacting magnesium hydroxide and carbonic acid gas. Examples of the liquid-liquid method include a method in which an acid (such as hydrochloric acid or sulfuric acid) and a base (such as sodium hydroxide or potassium hydroxide) are reacted by neutralization; a method in which an inorganic salt is reacted with an acid or a base; or a method in which inorganic salts are reacted with each other. For example, barium sulfate can be obtained by reacting barium hydroxide with sulfuric acid, aluminum hydroxide can be obtained by reacting aluminum sulfate with sodium hydroxide, and inorganic particles in which calcium and aluminum are complexed can be obtained by reacting calcium carbonate with aluminum sulfate. In synthesizing inorganic particles in this manner, any metal or metal compound can coexist in a reaction liquid. In such a case, the metal or metal compound can be efficiently incorporated into and complexed with the inorganic particles. For example, in a case where phosphoric acid is added to calcium carbonate to synthesize calcium phosphate, composite particles of calcium phosphate and titanium can be obtained by causing titanium dioxide to coexist in the reaction liquid.

As one preferable aspect, an average primary particle diameter of the inorganic particles can be, for example, 1 µm or less. Alternatively, it is possible to use inorganic particles having an average primary particle diameter of 500 nm or less, inorganic particles having an average primary particle diameter of 200 nm or less, inorganic particles having an average primary particle diameter of 100 nm or less, and inorganic particles having an average primary particle diameter of 50 nm or less. The average primary particle diameter of inorganic particles can be 10 nm or more. Note that the average primary particle diameter can be calculated based on electron micrography.

In addition, inorganic particles having various sizes and shapes can be complexed with fibers into composite fibers by adjusting the condition for synthesizing inorganic particles. For example, it is possible to provide composite fibers in which fibers are complexed with scale-shaped inorganic particles. A shape of inorganic particles constituting the composite fibers can be confirmed by observation with use of an electron microscope.

The inorganic particles can have a form of secondary particles obtained by aggregation of fine primary particles. Such secondary particles can be generated by a ripening process depending on a purpose of use. The aggregate can be made smaller by pulverization. Examples of a pulverizing method include a ball mill, a sand grinder mill, an impact mill, a high-pressure homogenizer, a low-pressure homogenizer, a Dinomill, an ultrasonic mill, a Kanda grinder, an attritor, a stone mill, a vibrating mill, a cutter mill, a jet mill, a disintegrator, a beating machine, a short-screw extruder, a twin-screw extruder, an ultrasonic stirrer, a household juicer mixer, and the like.

[Fibers]

The fibers constituting the composite fibers are preferably, for example, cellulosic fibers. Examples of the raw material of cellulosic fibers include pulp fibers (wood pulp and non-wood pulp), cellulose nanofibers, bacterial cellulose, animal-derived cellulose such as ascidian, and algae, and the wood pulp can be produced by converting wood feedstock into pulp. Examples of the wood feedstock include coniferous trees such as Japanese red pine, Japanese black pine, Sakhalin fir, Yezo spruce, Pinus koraiensis, Japanese larch, Japanese fir, Southern Japanese hemlock, Japanese cedar, Hinoki cypress, Japanese larch, Abies veitchii, spruce, Hinoki cypress leaf, Douglas fir, hemlock, white fir, spruce, Balsam fir, cedar, pine, Merkusii pine, and Radiata pine, and admixtures thereof; and broadleaf trees such as Japanese beech, birch, Japanese alder, oak, Machilus thunbergii, Castanopsis, Japanese white birch, Japanese aspen, poplar, Japanese ash, Japanese poplar, eucalyptus, mangrove, lauan, and acacia, and admixtures thereof.

A method for converting the natural material such as wood feedstock (woody raw material) into pulp is not particularly limited, and, for example, a pulping method commonly used in the paper industry can be employed. Wood pulp can be classified depending on the pulping method, for example, chemical pulp digested by a kraft method, a sulfite method, the soda method, a polysulfide method, or the like; mechanical pulp obtained by pulping with mechanical force such as a refiner, a grinder, or the like; semi-chemical pulp obtained by pulping with mechanical force after pretreatment with chemicals; wastepaper pulp; deinked pulp; and the like. The wood pulp can be unbleached (i.e., before bleaching) or bleached (i.e., after bleaching).

Examples of the non-wood pulp include cotton, hemp, sisal hemp, Manila hemp, flax, straw, bamboo, bagasse, kenaf, sugar cane, corn, rice straw, paper mulberry, paper bush, and the like.

The pulp fibers can be either unbeaten or beaten, and can be selected according to physical properties of the composite fibers. It is preferable that the pulp fibers are beaten. By the beating, it is possible to expect improvement in strength and promotion of fixing of inorganic particles to the pulp fibers.

These cellulose raw materials can also be further processed to be used as pulverized cellulose, chemically denatured cellulose such as oxidized cellulose, and cellulose nanofibers: CNF (microfibrillated cellulose: MFC, TEMPO-oxidized CNF, phosphoric acid esterified CNF, carboxymethylated CNF, mechanically pulverized CNF, and the like). The pulverized cellulose used in an aspect of the present invention includes both cellulose that is generally called powdered cellulose and the mechanically pulverized CNF. As the powdered cellulose, for example, it is possible to use (i) powdered cellulose produced by mechanically pulverizing carefully selected untreated pulp or crystalline cellulose powder that has a fixed particle size distribution, is in a rod-like shape, and is produced by refining, drying, pulverizing and sieving undecomposed residues obtained after acid hydrolysis, or (ii) commercially available products such as KC Flock (manufactured by Nippon Paper Industries, Co. Ltd.), CEOLUS (manufactured by Asahi Kasei Chemicals Corporation) and Avicel (manufactured by FMC). A degree of polymerization of cellulose in the powdered cellulose is preferably approximately 100 to 1500, a degree of crystallinity of the powdered cellulose by X-ray diffractometry is preferably 70% to 90%, and a volume average particle diameter measured by a laser diffraction particle size distribution measuring device is preferably 1 µm to 100 µm. The oxidized cellulose used in an aspect of the present invention can be obtained, for example, by oxidation in water with an oxidant in the presence of N-oxyl compound and a compound selected from the group consisting of bromide, iodide and a mixture thereof. The cellulose nanofibers can be obtained by a method of fibrillating the cellulose raw material. Examples of the fibrillating method include a method in which a water suspension or the like of cellulose or chemically denatured cellulose such as oxidized cellulose is mechanically ground or beaten with use of a refiner, a high-pressure homogenizer, a grinder, a uniaxial or multi-axial kneader, a bead mill, or the like, so that the cellulose or chemically denatured cellulose is fibrillated. One or more of the above methods can be combined to produce cellulose nanofibers. A fiber diameter of the produced cellulose nanofibers can be confirmed by electron microscopy or the like, and ranges, for example, from 5 nm to 1000 nm, preferably from 5 nm to 500 nm, more preferably from 5 nm to 300 nm. In producing the cellulose nanofibers, it is possible that an optional compound is further added to react with the cellulose nanofibers to modify a hydroxyl group, before and/or after the cellulose is fibrillated and/or made finer. Examples of modifying functional groups include an acetyl group, an ester group, an ether group, a ketone group, a formyl group, a benzoyl group, acetal, hemiacetal, oxime, isonitrile, allene, a thiol group, a urea group, a cyano group, a nitro group, an azo group, an aryl group, an aralkyl group, an amino group, an amide group, an imido group, an acrylyl group, a methacryloyl group, a propionyl group, a propioloyl group, a butyryl group, a 2-butyryl group, a pentanoyl group, a hexanoyl group, a heptanoyl group, an octanoyl group, a nonanoyl group, a decanoyl group, an undecanoyl group, a dodecanoyl group, a myristoyl group, a palmitoyl group, a stearoyl group, a pivaloyl group, a benzoyl group, a naphthoyl group, a nicotinoyl group, an isonicotinoyl group, a furoyl group, an acyl group such as a cinnamoyl group, an isocyanate group such as a 2-methacryloyloxyethyl isocyanoyl group, a methyl group, an ethyl group, a propyl group, a 2-propyl group, a butyl group, a 2-butyl group, a tert-butyl group, a pentyl group, a hexyl group, a heptyl group, an octyl group, a nonyl group, a decyl group, an undecyl group, a dodecyl group, a myristyl group, a palmityl group, an alkyl group such as a stearyl group, an oxirane group, an oxetane group, an oxyl group, a thiirane group, a thietane group, and the like. Hydrogens in these substituents can be substituted with a functional group such as a hydroxyl group or a carboxy group. Moreover, a part of alkyl group can be an unsaturated bond. A compound used to introduce these functional groups is not particularly limited, and examples of such a compound include a compound having a group derived from phosphoric acid, a compound having a group derived from carboxylic acid, a compound having a group derived from sulfuric acid, a compound having a group derived from sulfonic acid, a compound having an alkyl group, a compound having a group derived from amine, and the like. The compound having the phosphoric acid group is not particularly limited, and examples of such a compound include phosphoric acid, and lithium dihydrogen phosphate, dilithium hydrogen phosphate, trilithium phosphate, lithium pyrophosphate, and lithium polyphosphate which are lithium salts of phosphoric acid. Further, examples of the compound having the phosphoric acid group include sodium dihydrogen phosphate, disodium hydrogen phosphate, trisodium phosphate, sodium pyrophosphate, and sodium polyphosphate, which are sodium salts of phosphoric acid. Further, examples of the compound having the phosphoric acid group include potassium dihydrogen phosphate, dipotassium hydrogen phosphate, tripotassium phosphate, potassium pyrophosphate, and potassium polyphosphate, which are potassium salts of phosphoric acid. Further, examples of the compound having the phosphoric acid group include ammonium dihydrogen phosphate, diammonium hydrogen phosphate, triammonium phosphate, ammonium pyrophosphate, ammonium polyphosphate, and the like which are ammonium salts of phosphoric acid. Among these, phosphoric acid, sodium salts of phosphoric acid, potassium salts of phosphoric acid, and ammonium salts of phosphoric acid are preferable, and sodium dihydrogen phosphate and disodium hydrogen phosphate are more preferable, from the viewpoint of efficient introduction of the phosphoric acid group and easy industrial application. Note, however, that the compound having the phosphoric acid group is not particularly limited. The compound having carboxyl group is not particularly limited, and examples of the compound include dicarboxylic acid compounds such as maleic acid, succinic acid, phthalic acid, fumaric acid, glutaric acid, adipic acid, and itaconic acid, and tricarboxylic acid compounds such as citric acid, and aconitic acid. An acid anhydride of the compound having carboxyl group is not particularly limited, and examples of the acid anhydride include acid anhydrides of dicarboxylic acid compounds such as maleic anhydride, succinic anhydride, phthalic anhydride, glutaric anhydride, adipic anhydride, and itaconic anhydride. A derivative of the compound having carboxyl group is not particularly limited, and examples of the derivative includes an imide compound of acid anhydride of the compound having carboxyl group and a derivative of acid anhydride of the compound having carboxyl group. The imide compound of acid anhydride of the compound having carboxyl group is not particularly limited, and examples of the imide compound include imide compounds of dicarboxylic acid compounds such as maleimide, succinimide, and phthalic imide. A derivative of acid anhydride of the compound having carboxyl group is not particularly limited. Examples of the derivative include those in which at least part of hydrogen atoms of an acid anhydride of the compound having carboxyl group (such as dimethylmaleic anhydride, dimethylmaleic anhydride, and diphenylmaleic anhydride) are substituted with a substituent (e.g., an alkyl group, a phenyl group, and the like). Among the compound having a group derived from carboxylic acid, maleic anhydride, succinic anhydride, and phthalic anhydride are preferable because those are easily applied industrially and easily gasified. Note, however, that the compound having a group derived from carboxylic acid is not particularly limited. Alternatively, the cellulose nanofibers can be modified in a manner in which a modifying compound is physically adsorbed onto the cellulose nanofibers, without being chemically bound to the cellulose nanofibers. The compound to be physically adsorbed includes a surfactant or the like, and any one of anionic surfactant, cationic surfactant, and nonionic surfactant can be used. In a case where the modification is carried out with respect to the cellulose prior to fibrillating and/or pulverizing the cellulose, it is possible that those functional groups are desorbed after the fibrillating and/or pulverizing so that the original hydroxyl group is restored. By subjecting the cellulose to such modification, it is possible to facilitate fibrillation of the cellulose nanofibers and to make it easier to mix the cellulose nanofibers with various materials.

It is possible to employ various natural fibers, synthetic fibers, semi-synthetic fibers, or inorganic fibers, other than cellulosic fibers. Examples of the natural fibers include, for example, protein-based fibers such as wool fibers, silk fibers, and collagenous fibers, complex sugar chain fibers such as chitin/chitosan fibers and algin fibers, and the like. Examples of the synthetic fibers include polyester, polyamide, polyolefin, and acrylic fibers, and the like. Examples of the semi-synthetic fibers include rayon, lyocell, acetate, and the like. Examples of the inorganic fibers include glass fibers, carbon fibers, various metal fibers, and the like.

Moreover, composite fibers of synthetic fibers and cellulosic fibers can also be used in an aspect of the present invention and, for example, composite fibers composed of cellulosic fibers and polyester, polyamide, polyolefin, acrylic fibers, glass fibers, carbon fibers, various metal fibers, or the like can be used.

Among those examples indicated above, the fibers preferably include wood pulp or a combination of wood pulp and non-wood pulp and/or synthetic fibers, more preferably include wood pulp alone.

In a preferable aspect, fibers constituting the composite fibers are pulp fibers. For example, a fibrous substance recovered from paper mill wastewater can be supplied to a carbonation reaction in an aspect of the present invention. By supplying such a substance to a reaction tank, various composite particles can be synthesized and also, in terms of shape, fibrous particles or the like can be synthesized.

Moreover, in addition to the fibers, substances can be used which do not directly participate in synthetic reaction of inorganic particles but are incorporated into produced inorganic particles to form composite particles. For example, in an aspect in which fibers such as pulp fibers are used, it is possible to synthesize inorganic particles in a solution containing inorganic particles, organic particles, a polymer, and the like in addition to the pulp fibers, and thus composite particles can be produced into which those substances are incorporated.

The above exemplified fibers can be used alone or two or more types of those fibers can be used in combination.

A fiber length of the fibers to be complexed is not particularly limited and an average fiber length can be, for example, approximately 0.1 µm to 15 mm, 1 µm to 12 mm, 100 µm to 10 mm, 500 µm to 8 mm, or the like.

An amount of fibers to be complexed is preferably an amount with which 15% or more of the fiber surface is covered with inorganic particles. For example, a weight ratio between fibers and inorganic particles is preferably 5/95 to 95/5, and can be 10/90 to 90/10, 20/80 to 80/20, 30/70 to 70/30, 40/60 to 60/40.

Production Example 1 of Composite Fibers:
Synthesis of Composite Fibers Composed of
Calcium Carbonate and Cellulosic Fibers Next, as an example of a method for producing composite fibers, an example will be described in which composite fibers are synthesized from calcium carbonate and cellulosic fibers.

By synthesizing inorganic particles in a solution containing cellulosic fibers, it is possible to synthesize composite fibers. The method for synthesizing inorganic particles can be a known method. In a case where calcium carbonate is synthesized, the calcium carbonate can be synthesized by, for example, a carbon dioxide process, a soluble salt reaction method, a lime-soda process, a soda method, or the like. In a preferable aspect, calcium carbonate is synthesized by the carbon dioxide process.

In general, in a case where calcium carbonate is produced by the carbon dioxide process, lime is used as a calcium source, and calcium carbonate is synthesized by a slaking step of obtaining slaked lime $Ca(OH)_2$ by adding water to quick lime CaO and a carbonation step of obtaining calcium carbonate $CaCO_3$ by blowing a carbonic acid gas $CO_2$ into the slaked lime. In this case, it is possible to eliminate poorly soluble lime particles contained in a slaked lime suspension (prepared by adding water to quick lime) by passing the suspension through a screen. Alternatively, slaked lime can be directly employed as a calcium source. In a case where calcium carbonate is synthesized by the carbon dioxide process in an aspect of the present invention, the carbonation reaction can be carried out in the presence of cavitation bubbles.

In general, as a reactor vessel (carbonator) for producing calcium carbonate by the carbon dioxide process, a gas blowing type carbonator and a mechanical stirring type carbonator are known. Among these, the mechanical stirring type carbonator is more preferable. The mechanical stirring type carbonator is provided with a stirrer that is placed inside a carbonator. A carbonic acid gas is introduced near the stirrer, and thus fine gas bubbles of the carbonic acid gas are generated. By this mechanism, it is easy to control a size of gas bubbles uniformly and finely. From this, efficiency of reaction between the slaked lime and the carbonic acid gas is improved (see "Cement•Sekkou•Sekkai Handbook (*Handbook of cement, gypsum, and lime*)", Gihodo Shuppan Co., Ltd., 1995, page 495). In the gas blowing type carbonator, a carbonic acid gas is blown into a carbonation reactor vessel containing a slaked lime suspension (milk of lime) so that the slaked lime is caused to react with the carbonic acid gas.

It is more preferable that calcium carbonate is synthesized in the presence of cavitation bubbles. This is because, even in a case where resistance of a reaction liquid increases due to high concentration of the reaction liquid or progression of carbonation reaction, the carbonic acid gas can be made finer by sufficiently stirring the carbonic acid gas. From this, it is possible to precisely control carbonation reaction, and it is accordingly possible to prevent energy loss. Residues of screened lime which are poorly soluble precipitate fast and tend to constantly remain at the bottom. However, by carrying out the synthesis in the presence of cavitation bubbles, it is possible to prevent a gas blowing port from being clogged.

Therefore, it is possible to efficiently progress the carbonation reaction, and thus uniform calcium carbonate fine particles can be produced. In particular, by using jet cavitation, it is possible to carry out sufficient stirring without a mechanical stirrer such as a blade. It is also possible to use a conventionally known reactor vessel. Of course, the above described gas blowing type carbonator or mechanical stirring type carbonator can be adequately used. Each of those vessels can be used in combination with jet cavitation using a nozzle or the like.

In a case where calcium carbonate is synthesized by the producing method of carbonic acid gas, a solid concentration of an aqueous suspension of slaked lime is preferably not less than 0.1% by weight, more preferably not less than 0.5% by weight, further preferably not less than 1% by weight, from the viewpoint of achieving better reaction efficiency and reducing a production cost. Moreover, the solid concentration is preferably not more than 40% by weight, more preferably not more than 30% by weight, further preferably not more than 20% by weight, or the like from the viewpoint of achieving better reaction efficiency by carrying out the reaction in a state of better fluidity. According to an aspect in which calcium carbonate is synthesized in the presence of cavitation bubbles, it is possible to more suitably mix the reaction liquid and the carbonic acid gas even with use of a suspension (slurry) having a higher solid concentration.

As the aqueous suspension containing slaked lime, it is possible to use an aqueous suspension that is generally used in synthesizing calcium carbonate. For example, such an aqueous suspension can be prepared by mixing slaked lime with water, slaking (digesting) quick lime (calcium oxide) with water, or the like. Conditions in slaking are not particularly limited and, for example, a concentration of CaO can be not less than 0.1% by weight, preferably not less than 1% by weight, and a temperature can be 20° C. to 100° C., preferably 30° C. to 100° C. An average residence time in a slaking reaction tank (i.e., slaker) is also not particularly limited and can be, for example, 5 minutes to 5 hours, preferably within 2 hours. Of course, the slaker can be of either a batch type or a continuous type. Note that the carbonation reactor vessel (i.e., carbonator) and the slaking reaction tank (i.e., slaker) can be provided separately, or one reaction tank can be used as the carbonation reactor vessel and the slaking reaction tank.

Production Example 2 of Composite Fibers:
Synthesis of Composite Fibers Composed of
Barium Sulfate and Cellulosic Fibers Next, as an example of a method for producing composite fibers, an example will be described in which composite fibers are synthesized from barium sulfate and cellulosic fibers.

Composite fibers composed of barium sulfate and cellulosic fibers can be produced by synthesizing barium sulfate in a solution in the presence of cellulosic fibers. Examples of the method include a method in which an acid (such as sulfuric acid) and a base are reacted by neutralization; a method in which an inorganic salt is caused to react with an acid or a base; or a method in which inorganic salts are caused to react with each other. For example, barium sulfate can be obtained by causing barium hydroxide to react with sulfuric acid or aluminum sulfate. Alternatively, barium sulfate can be caused to precipitate by adding barium chloride to an aqueous solution that contains sulfate. The composite fibers composed of barium sulfate and cellulosic fibers can be suitably used as a radiation-proof material. Moreover, according to the method for producing barium sulfate described in this example, aluminum hydroxide is also generated. Barium sulfate and aluminum hydroxide are excellent in function to impart flame retardancy. Therefore, the composite fibers obtained in this example, and further the composition can be suitably used for meeting an expectation of flame retardancy.

Production Example 3 of Composite Fibers:
Synthesis of Composite Fibers Composed of
Hydrotalcite and Cellulosic Fibers Next, as an example of a method for producing composite fibers, an example will be described in which composite fibers are synthesized from hydrotalcite and cellulosic fibers. In a case where the inorganic particles constituting the composite fibers are hydrotalcite, it is possible to produce composite fibers composed of hydrotalcite and fibers by synthesizing hydrotalcite in a solution in the presence of fibers.

The method for synthesizing hydrotalcite can be a known method. For example, in a reactor vessel, fibers are immersed in (i) an aqueous carbonate solution containing carbonate ions that form an intermediate layer and (ii) an alkaline solution (such as sodium hydroxide), and then an acid solution (which is an aqueous metal salt solution containing bivalent metal ions and trivalent metal ions which form a base layer) is added. Then, coprecipitation reaction is carried out while controlling a temperature, pH, and the like, and thus hydrotalcite is synthesized. Alternatively, in a reactor vessel, fibers are immersed in an acid solution (which is an aqueous metal salt solution containing bivalent metal ion and trivalent metal ions which form a base layer), and then an aqueous carbonate solution containing carbonate ions which form an intermediate layer and an alkaline solution (such as sodium hydroxide) are dripped. Then, coprecipitation reaction is carried out while controlling a temperature, pH, and the like, and thus hydrotalcite can be synthesized. The reaction is generally carried out at normal atmospheric pressure. Alternatively, hydrotalcite can be obtained by hydrothermal reaction using an autoclave or the like (Japanese Patent Application Publication Tokukai-sho No. 60-6619 (1985)).

As a source of bivalent metal ions that form the base layer, it is possible to use a chloride, sulfide, nitrate, or sulfate of magnesium, zinc, barium, calcium, iron, copper, silver, cobalt, nickel, or manganese. As a source of trivalent metal ions that form the base layer, it is possible to use a chloride, sulfide, nitrate, or sulfate of aluminum, iron, chromium, or gallium.

In a case where one of precursors of inorganic particles is alkaline as in this example, the fibers can be swollen by dispersing the fibers in advance in a solution of the alkaline precursor, so that the composite fibers composed of inorganic particles and fibers can be efficiently obtained. For example, the reaction can be started after swelling of the fibers is facilitated by stirring the mixture for 15 minutes or more after mixing, or the reaction can be started immediately after the mixing. In a case where a substance such as aluminum sulfate (aluminum sulfide, polyaluminum chloride, or the like) that is more likely to interact with cellulose is used as a part of the precursor of inorganic particles, a ratio at which the inorganic particles are fixed to the fibers can be improved by mixing the aluminum sulfate with the fibers in advance.

[Inorganic Particles Different in Type from Inorganic Particles Constituting the Composite Fibers]

The composition in accordance with an aspect of the present invention can contain different-type inorganic particles that are different in type from the inorganic particles constituting the composite fibers. In a case where the inorganic particles constituting the composite fibers and the different-type inorganic particles have similar functions, such functions can be further improved. Alternatively, in a case where the inorganic particles constituting the composite fibers and the different-type inorganic particles have different functions, it is possible to provide a composition that has both the functions.

The different-type inorganic particles which are different in type from the inorganic particles constituting the composite fibers can be selected as appropriate in accordance with a purpose of use of the composition. For example, in a case of seeking improvement of opacity, it is preferable to use titanium oxide, kaoline, calcium carbonate, talc, or silica as the different-type inorganic particles. In particular, in a case where the inorganic particles of the composite fibers are hydrotalcite and the different-type inorganic particles are titanium oxide, it is possible to further improve opacity. Specifically, the different-type inorganic particles only need to be different in type from the inorganic particles constituting the composite fibers, and the foregoing descriptions of the inorganic particles constituting the composite fibers are also applicable to the different-type inorganic particles. As the different-type inorganic particles, it is possible to use a compound that contains a metal. Examples of such a compound include a compound containing at least one metal selected from the group consisting of gold, silver, copper, titanium, platinum, iron, zinc, and aluminum. A simple substance of gold, silver, copper, titanium, zinc, or aluminum or a compound that contains any of those substances as ions particularly excels in deodorizing function, and it is therefore possible to impart the excellent deodorizing function to the composition. From the viewpoint of imparting an excellent deodorizing function to the composition, it is more preferable to use a simple substance of silver or copper, or a compound that contains silver or copper as ions.

In a case where the composition in accordance with an aspect of the present invention contains different-type inorganic particles which are different in type from the inorganic particles constituting the composite fibers, a weight ratio between the composite fibers and the different-type inorganic particles can be set as appropriate and is preferably, for example, 99/1 to 70/30. The effect may be brought about with a small amount of the different-type inorganic particles when, for example, silver, copper, or the like is used. Depending on the purpose of use, it is sometimes necessary to add a large amount of the different-type inorganic particles. A good yield can be achieved by setting an added amount of the different-type inorganic particles to 30% or less.

[Fibers Different in Type from Fibers Constituting the Composite Fibers]

The composition in accordance with an aspect of the present invention can contain different-type fibers that are different in type from the fibers constituting the composite fibers. In a case where the fibers constituting the composite fibers and the different-type fibers have similar functions, such functions can be further improved. Alternatively, in a case where the fibers constituting the composite fibers and the different-type fibers have different functions, it is possible to provide a composition that has both the functions. Alternatively, in a case where the fibers constituting the composite fibers and the different-type inorganic particles have different functions, it is possible to provide a composition that has both the functions.

The different-type fibers which are different in type from fibers constituting the composite fibers can be selected as appropriate in accordance with a purpose of use of the composition. Specifically, the different-type fibers only need to be different in type from the fibers constituting the composite fibers, and the foregoing descriptions of the fibers constituting the composite fibers are also applicable to the different-type fibers.

The different-type fibers which are different in type from fibers constituting the composite fibers can be fibers which are carrying an intended compound. For example, it is possible to employ metal-carrying fibers, fibers carrying zeolite, or fibers carrying an inorganic substance. The metal-carrying fibers are fibers that are carrying a simple metal and/or a compound containing a metal. The metal which the fibers carry can be selected as appropriate in accordance with a purpose of use of the composition. Examples of such a metal include a compound containing at least one metal selected from the group consisting of gold, silver, copper, titanium, platinum, iron, zinc, and aluminum. A simple substance of gold, silver, copper, titanium, zinc, or aluminum or a compound that contains any of those substances as ions particularly excels in deodorizing function, and it is therefore possible to impart the excellent deodorizing function to the composition. From the viewpoint of imparting the excellent deodorizing function to the composition, it is more preferable to use cellulosic fibers carrying copper. In addition, the foregoing examples of metal described as the inorganic particles constituting the composite fibers are also applicable to the metal for use in the metal-carrying fibers.

The foregoing descriptions of the fibers constituting the composite fibers are also applicable to a type of fibers to carry a metal, zeolite, or another inorganic substance.

In a case where the composition in accordance with an aspect of the present invention contains different-type fibers which are different in type from the fibers constituting the composite fibers, a weight ratio between the composite fibers and the different-type fibers can be set as appropriate and is preferably, for example, 99/1 to 5/90. In a case where other fibers are used as an assistant, the composite fibers may be used in a proper amount as a main component. On the contrary, in a case where composite fibers that highly brings about an effect is diluted and used (and other fibers are ordinary LBKP or the like), an amount of such composite fibers can be small.

Production Example 1 of Fibers Different in Type from Fibers Constituting the Composite Fibers: Synthesis of Metal-Carrying Cellulosic Fibers Next, as an example of a method for producing fibers different in type from fibers constituting the composite fibers, an example will be described in which composite fibers are synthesized from metal-carrying cellulosic fibers.

Sanitary tissue paper in accordance with an embodiment of the present invention is constituted by metal-carrying cellulosic fibers that are obtained by introducing one or more metal elements selected from the group consisting of Ag, Au, Pt, Pd, Mn, Fe, Ti, Al, Zn and Cu into oxidized cellulosic fibers whose surfaces have a carboxyl group or a carboxylate group.

The metal-carrying cellulosic fibers can be obtained by bringing an aqueous metal compound solution into contact with oxidized cellulosic fibers in which a carboxyl group or a carboxylate group has been introduced into cellulosic fiber surfaces. A method for producing the sanitary tissue paper in accordance with an embodiment of the present invention can be, for example, a method in which the aqueous metal compound solution is brought into contact with a sheet made from a raw material containing oxidized cellulosic fibers or a method in which oxidized cellulosic fibers are carrying a metal in advance and then a sheet is made from a raw material containing the metal-carrying cellulosic fibers obtained above.

The oxidized cellulosic fibers can be produced by oxidizing cellulosic fibers such as wood pulp with use of an N-oxyl compound as a catalyst. By this oxidation reaction, a primary hydroxyl group at C6 position in a glucopyranose ring of the cellulose surface is selectively oxidized, and thus oxidized cellulosic fibers can be obtained which have a carboxyl group or a carboxylate group on their surfaces. Cellulose used as the raw material is preferably native cellulose. The oxidation reaction is preferably carried out in water. A concentration of cellulosic fibers in the reaction is not particularly limited, and is preferably not more than 5% by mass. An amount of the N-oxyl compound can be approximately 0.1 mmol/L to 4 mmol/L with respect to the reaction system. In the reaction, a publicly known co-oxidant can be used. Examples of the co-oxidant include hypohalous acid and salt thereof. An amount of the co-oxidant is preferably 1 mol to 40 mol with respect to 1 mol of the N-oxyl compound.

The reaction temperature is preferably 4° C. to 40° C., more preferably the room temperature. pH of the reaction system is preferably 8 to 11. A degree of oxidation can be adjusted as appropriate by adjusting a reaction time, an amount of the N-oxyl compound, and the like.

In the oxidized cellulosic fibers obtained as above described, acid groups exist in the surfaces, and acid groups hardly exist inside the fibers. This may be because the cellulosic fibers are crystalline and therefore the oxidant is less likely to diffuse inside the fibers.

The carboxyl group is a group represented by —COOH, and the carboxylate group is a group represented by —COO—. Counter ion(s) for the carboxylate group in producing the oxidized cellulosic fibers are not particularly limited. Ions of a later described metal are substituted by the counter ions, and an ionic bond with the carboxylate group is formed. The carboxyl group seems to coordinate with, for example, metal ions such as copper ions. The carboxyl group and the carboxylate group are also collectively referred to as "acid group".

An acid group content can be measured by a method disclosed in paragraph [0021] of Japanese Patent Application Publication Tokukai No. 2008-001728. That is, 60 mL of slurry containing 0.5% by mass to 1% by mass of a precisely weighed dry cellulose sample is prepared, and pH is adjusted to approximately 2.5 by use of 0.1 mol/L of a hydrochloric acid solution. After that, conductimetry is carried out by dripping 0.05 mol/L of an aqueous sodium hydroxide solution. The measurement is continued until the pH becomes approximately 11. An acid group amount X1 is obtained using the following formula based on a sodium hydroxide amount (V) that has been consumed until a level of weak acid neutralization is exhibited at which change in electric conductivity is gentle.

$$X1\ (mmol/g) = V\ (mL) \times 0.05 / mass\ of\ cellulose\ (g)$$

An amount of acid group in the cellulosic fibers is preferably 0.2 mmol/g to 2.2 mmol/g. In a case where the amount of acid group is 0.2 mmol/g or more, a sufficient amount of metal ions exist in the cellulosic fiber surface, and a deodorizing function is appropriately achieved. In a case where the amount of acid group is 2.2 mmol/g or less, good drainage property in making sanitary tissue paper is maintained, and it is therefore possible to reduce a dehydration load.

Next, an aqueous solution containing a compound of the metal is brought into contact with the oxidized cellulosic fibers, and metal ions derived from the metal compound form an ionic bond with the carboxylate group. Note that the carboxyl group seems to be ionized and form an ionic bond with metal ions via a carboxylate group, or seems to coordinate with metal ions as above described.

The aqueous metal compound solution is an aqueous solution of metal salt. Examples of the metal salt include complex (complex ion), halide, nitrate, sulfate, and acetate. The metal salt is preferably water soluble.

In regard to the method for contacting the metal compound, it is possible that a dispersion solution of cellulosic fibers prepared in advance is mixed with the aqueous metal compound solution or it is possible that a film is formed by applying a dispersion solution containing cellulosic fibers to a base material, and then the film is impregnated with the aqueous metal compound solution. In this case, the film can be fixed on the substrate or can be in a state of being detached from the substrate.

A concentration of the aqueous metal compound solution is not particularly limited, and is preferably 0.2 mmol to 2.2 mmol, more preferably 0.4 mmol to 1.8 mmol, with respect to 1 g of cellulosic fibers.

A time of contacting with the metal compound can be adjusted as appropriate. A temperature in contacting is not particularly limited, and is preferably 20° C. to 40° C. pH of the solution in contacting is not particularly limited, and is preferably 7 to 13, particularly preferably 8 to 12, because metal ions are less likely to bind to the carboxyl group if pH is lower.

Whether the oxidized cellulosic fibers contain metal ions (i.e., whether metal ions coordinate) can be confirmed by a scanning electron microscopic image and ICP emission spectrometry on an extraction liquid using strong acid. That is, the presence of metal ions cannot be confirmed by the scanning electron microscopic image, whereas whether the metal is contained can be confirmed by the ICP emission spectrometry. Meanwhile, for example, in a case where the metal is reduced from ions and exists as metal particles, the metal particles can be confirmed based on the scanning electron microscopic image, and it is therefore possible to determine whether or not metal ions exist. Whether or not metal ions exit can also be determined based on the scanning electron microscopic image and elemental mapping. That is, metal ions cannot be confirmed by the scanning electron microscopic image but whether or not metal ions exist can be confirmed by elemental mapping.

By using one or more ions selected from the group consisting of Ag and Cu as the metal ion, an antibacterial function is imparted. Meanwhile, it is not necessary that the metal particles bind to all the acid groups of the cellulosic fibers, and the remaining acid group can also neutralize an odor component such as ammonia, and thus a deodorizing function is brought about.

[Organic Particles]

The composition in accordance with an aspect of the present invention can contain organic particles. The organic particles are an organic compound in a particulate form. Examples of the organic particles include flame retardant organic materials (such as of phosphoric acid base or boron base) for enhancing flame retardancy, urea-formalin resin, polystyrene resin, phenol resin, hollow fine particles, acrylamide composite fibers, wood-derived substances (filaments, microfibrils, powdered kenaf), denatured insoluble starch for improving printability, ungelatinized starch, latex, and the like.

In a case where the composition in accordance with an aspect of the present invention contains organic particles, a weight ratio between the composite fibers and the organic particles can be set as appropriate and is preferably, for example, 99/1 to 70/30. A good yield can be achieved by setting an added amount of the organic particles to 30% or less.

[Method for Producing Composition]

In the method for producing the composition in accordance with an aspect of the present invention, it is only necessary that the above described composite fibers are mixed with at least one of (i) different-type inorganic particles which are different in type from the inorganic particles constituting the composite fibers, (ii) different-type fibers which are different in type from fibers constituting the composite fibers, and (iii) organic particles.

As a mixing method, for example, it is possible to mix the solution of composite fibers with components other than the composite fibers, i.e., the components such as the different-type inorganic particles which are different in type from the inorganic particles constituting the composite fibers, the different-type fibers which are different in type from fibers constituting the composite fibers, and/or the organic particles. The solution of the composite fibers can be, for example, a solution of composite fibers which is obtained when composite fibers are produced by a method in which inorganic particles are synthesized in a fiber solution. After the solution of the composite fibers is mixed with components different from the composite fibers, the solution can be molded as appropriate.

[Form of Composition]

The composition in accordance with an aspect of the present invention can be used in any of various shapes such as of, for example, powder, pellets, molded product, aqueous suspension, paste, and sheet. Alternatively, it is possible to employ a molded product or a molded article of particles, pellets, or the like which contains the composition in accordance with an aspect of the present invention as a main component and other materials. A dryer that is used to dry the composition into powder is not particularly limited and, for example, an airflow dryer, a band dryer, a spray dryer, or the like can be suitably used.

The composition in accordance with an aspect of the present invention can be used for a wide variety of applications. Examples of the applications include paper, fibers, cellulosic composite materials, filter materials, paints, plastics and other resins, rubbers, elastomers, ceramics, glasses, tires, building materials (such as asphalts, asbestos, cement, boards, concrete, bricks, tiles, plywood, and fiber boards), various carriers (such as catalytic carriers, pharmaceutical carriers, agrochemical carriers, and microbial carriers), adsorbents (for removing impurities, deodorization, dehumidification, and the like), wrinkle inhibitors, clays, abrasives, modifiers, repairing materials, heat insulating materials, dampproof materials, water-repellent materials, waterproof materials, light shielding materials, sealants, shielding materials, insect repellents, adhesive agents, inks, cosmetics, medical materials, paste materials, discoloration inhibitor, food additives, tablet excipients, dispersing agents, shape retaining agents, water retaining agents, filtration assistants, essential oil materials, oil processing agents, oil modifiers, radiowave absorptive materials, insulators, sound insulating materials, vibration proofing materials, semiconductor sealing material, radiation-proof materials, cosmetics, fertilizers, feeds, perfumes, additives for paints and adhesive agents, flame retardant materials, hygiene products (such as disposable diapers, sanitary napkins, incontinent pads, and breast milk pads), and the like. In addition, the composite can be used in various types of filler, coating agents, and the like in the above described applications.

The composition in accordance with an aspect of the present invention can be used in paper making applications. Examples of such paper making applications include printing paper, newspaper, inkjet paper, PPC paper, kraft paper, fine paper, coated paper, fine coating paper, wrapping paper, tissue paper, colored fine paper, cast coated paper, noncarbon paper, label paper, thermal paper, various kinds of fancy paper, water-soluble paper, release paper, process paper, base sheet for wallpaper, incombustible paper, flame retardant paper, base sheet for laminated plate, printed electronics paper, battery separator, cushion paper, tracing paper, impregnated paper, ODP paper, building paper, decorative material paper, envelope paper, tape paper, heat exchanging paper, chemical fiber paper, sterilization paper, waterproof paper, oil-proof paper, heat-resistant paper, photocatalytic paper, facial tissue (such as oil blotting paper), various kinds of sanitary paper (such as toilet paper, tissue, wiper, diaper, and sanitary goods), cigarette paper, paperboard (such as linerboard, corrugating medium, and white paperboard), paper plate base sheet, paper cup base sheet, baking paper, sand paper, synthetic paper, and the like.

In a case where the composition in accordance with an aspect of the present invention is used, various known assistants can be further added in addition to foregoing components. For example, a chelating agent can be added. Specific examples of the chelating agent include polyhydroxy carboxylic acid such as citric acid, malic acid, and tartaric acid; dicarboxylic acid such as oxalic acid; saccharic acid such as gluconic acid; aminopolycarboxylic acid such as iminodiacetic acid and ethylenediaminetetraacetic acid and alkali metal salts thereof; alkali metal salts of polyphosphoric acid such as hexametaphosphoric acid and tripolyphosphoric acid; amino acid such as glutamic acid and aspartic acid, and alkali metal salts thereof; ketones such as acetylacetone, methyl acetoacetate, allyl acetoacetate; saccharides such as cane sugar; polyol such as sorbitol; and the like. Moreover, it is possible to add a surface treatment agent. Examples of the surface treatment agent include saturated fatty acid such as palmitic acid and stearic acid, unsaturated fatty acid such as oleic acid and linoleic acid, resin acid such as alicyclic carboxylic acid and abietic acid, and salts, esters, and ethers thereof, an alcohol-based activator, sorbitan fatty acid esters, an amide-based surfactant, an amine-based surfactant, polyoxyalkylene alkylethers, polyoxyethylene nonylphenyl ether, sodium alpha olefin sulfonate, long-chain alkyl amino acid, amine oxide, alkylamine, quaternary ammonium salt, aminocarboxylic acid, phosphonic acid, polyvalent carboxylic acid, condensed phosphoric acid, and the like. Moreover, a dispersing agent can be optionally used. Examples of the dispersing agent include sodium polyacrylate, sucrose fatty acid ester, glycerin fatty acid ester, acrylic acid-maleic acid copolymer ammonium salt, a methacrylic acid-naphthoxypolyethylene glycol acrylate copolymer, methacrylic acid-polyethyleneglycol monomethacrylate copolymer ammonium salt, polyethyleneglycol monoacrylate, and the like. These can be used solely, or two or more of these can be used in combination. A point in time of adding such an additive can be prior to or after the synthetic reaction. Each of the assistants can be added in an amount of preferably 0.0001% to 10%, more preferably 0.001% to 5%, with respect to an amount of the inorganic particles to be synthesized.

In a case where the composition in accordance with an aspect of the present invention is used, particles generally called inorganic filler and organic filler, or various types of fibers (hereinafter, referred to as "fillers, etc.") can be used in addition to the foregoing components. Examples of the inorganic filler include calcium carbonate (light calcium carbonate, heavy calcium carbonate), magnesium carbonate, barium carbonate, aluminum hydroxide, calcium hydroxide, magnesium hydroxide, zinc hydroxide, active carbon, clay (kaoline, fired kaolin, Delaminated Kaolin), talc, zinc oxide, zinc stearate, titanium dioxide, silica composed of sodium silicate and mineral acid (white carbon, silica/calcium carbonate composite fibers, silica/titanium dioxide composite fibers), white clay, bentonite, diatomaceous earth, calcium sulfate, zeolite, an inorganic filler that is obtained by recycling ash obtained from a deinking process, an inorganic filler obtained by forming the composite fibers with silica or calcium carbonate during the process of recycling ash obtained from the deinking process. As the calcium carbonate-silica complex, in addition to the complexes of calcium carbonate and/or light calcium carbonate and silica, amorphous silica such as white carbon can be used in combination. Examples of the organic filler include urea-formalin resin, polystyrene resin, phenol resin, hollow fine particles, acrylamide composite fibers, wood-derived substances (filaments, microfibrils, powdered kenaf), denatured insoluble starch, ungelatinized starch, and the like. As the fibers, not only natural fibers such as cellulose, but also synthetic fibers that are artificially synthesized from a raw material such as petroleum, regenerated fibers (semi-synthetic fibers) such as rayon and lyocell, and inorganic fibers can be used without restrictions. Examples of the natural fibers include, in addition to the above ones, protein-based fibers such as wool fibers, silk fibers, and collagenous fibers, complex sugar chain fibers such as chitin/chitosan fibers and algin fibers, and the like. Examples of the raw material of cellulose-based fibers include pulp fibers (wood pulp and non-wood pulp), bacterial cellulose, animal-derived cellulose such as ascidian, and algae, and the wood pulp can be produced by converting wood feedstock into pulp. Examples of the wood feedstock include coniferous trees such as Japanese red pine, Japanese black pine, Sakhalin fir, Yezo spruce, Pinus koraiensis, Japanese larch, Japanese fir, Southern Japanese hemlock, Japanese cedar, Hinoki cypress, Japanese larch, Abies veitchii, spruce, Hinoki cypress leaf, Douglas fir, hemlock, white fir, spruce, Balsam fir, cedar, pine, Merkusii pine, and Radiata pine, and admixtures thereof; and broadleaf trees such as Japanese beech, birch, Japanese alder, oak, Machilus thunbergii, Castanopsis, Japanese white birch, Japanese aspen, poplar, Japanese ash, Japanese poplar, eucalyptus, mangrove, lauan, and acacia, and admixtures thereof. A method for converting the wood feedstock into pulp is not particularly limited and, for example, a pulping method commonly used in the paper industry can be employed. Wood pulp can be classified depending on the pulping method, for example, chemical pulp digested by a kraft method, a sulfite method, the soda method, a polysulfide method, or the like; mechanical pulp obtained by pulping with mechanical force such as a refiner, a grinder, or the like; semi-chemical pulp obtained by pulping with mechanical force after pretreatment with chemicals; wastepaper pulp; deinked pulp; and the like. The wood pulp can be unbleached (i.e., before bleaching) or bleached (i.e., after bleaching). Examples of the non-wood pulp include cotton, hemp, sisal hemp, Manila hemp, flax, straw, bamboo, bagasse, kenaf, sugar cane, corn, rice straw, paper mulberry, paper bush, and the like. Wood pulp and non-wood pulp can be either unbeaten or beaten. These cellulose raw materials can also be further processed to be used as pulverized cellulose such as powdered cellulose, chemically denatured cellulose such as oxidized cellulose, and cellulose nanofibers: CNF (microfibrillated cellulose: MFC, TEMPO-oxidized CNF, phosphoric acid esterified CNF, carboxymethylated CNF, mechanically pulverized CNF). Examples of the synthetic fibers include polyester, polyamide, polyolefin, and acrylic fibers. Examples of the semi-synthetic fibers include rayon and acetate, and the like. Examples of the inorganic fibers include glass fibers, carbon fibers, various metal fibers, and the like. The above exemplified fibers can be used alone or two or more types of those fibers can be used in combination. Each of the fillers, etc. can be added in an amount of preferably 0.001% to 20%, more preferably 0.1% to 10%, with respect to a mass of the fiber composite fibers.

Aspects of the present invention can also be expressed as follows:

The present invention encompasses but not limited to the following features:

(1) A composition including: composite fibers composed of inorganic particles and fibers; and at least one of (i) different-type inorganic particles which are different in type from the inorganic particles, (ii) different-type fibers which are different in type from the fibers, and (iii) organic particles.

(2) The composition described in (1) in which the different-type fibers are metal-carrying fibers.

(3) The composition described in (1) in which the different-type fibers are composite fibers composed of inorganic particles and fibers.

(4) The composition described in (2) in which a metal, which fibers carry in the metal-carrying fibers, includes a compound that contains at least one metal selected from the group consisting of gold, silver, titanium, copper, platinum, iron, zinc, and aluminum.

(5) The composition described in (1) in which the different-type inorganic particles include a compound containing at least one metal selected from the group consisting of gold, silver, titanium, copper, platinum, iron, zinc, and aluminum.

(6) The composition described in (1) in which the different-type inorganic particles include at least one compound selected from the group consisting of titanium oxide, calcium carbonate, magnesium carbonate, and aluminum hydroxide.

(7) The composition described in any one of (1) through (6) in which the fibers in the composite fibers are cellulosic fibers.

(8) The composition described in any one of (1) through (7) in which the inorganic particles in the composite fibers are hydrotalcite.

(9) The composition described in (8) in which ash of the composite fibers composed of hydrotalcite and fibers contains at least one of magnesium and zinc in an amount of not less than 10% by weight.

(10) The composition described in any one of (1) through (9) in which, in the composite fibers, 15% or more of a surface of each of the fibers is covered with the inorganic particles.

(11) The composition described in any one of (1) through (10) in which an average primary particle diameter of the inorganic particles in the composite fibers is 1 µm or less.

EXAMPLES

The present invention will be described below in more detail with reference to specific experiment examples. Note, however, that the present invention is not limited to such experiment examples. In addition, unless otherwise specified in this specification, concentrations, parts, and the like are based on the weight, and numerical ranges are described as including endpoints thereof.

Examples 1 and 2: Composition of Composite Fibers Composed of Hydrotalcite and Fibers and Copper-Carrying Pulp (1) Synthesis of Composite Fibers from Hydrotalcite and Fibers (1-1) Preparation of Alkaline Solution and Acid Solution A solution for synthesizing hydrotalcite (HT) was prepared. As an alkaline solution (solution A), a mixed aqueous solution was prepared which contained $Na_2CO_3$ (Wako Pure Chemical Industries, Ltd.) and NaOH (Wako Pure Chemical Industries, Ltd.) As an acid solution (solution B), a mixed aqueous solution was prepared which contained $ZnCl_2$ (Wako Pure Chemical Industries, Ltd.) and $AlCl_3$ (Wako Pure Chemical Industries, Ltd.)

Alkaline solution (solution A, $Na_2CO_3$ concentration: 0.05 M, NaOH concentration: 0.8 M)

Acid solution (solution B, Zn-base, $ZnCl_2$ concentration: 0.3 M, $AlCl_3$ concentration: 0.1 M)

(1-2) Synthesis of Composite Fibers

As fibers to be complexed, cellulosic fibers were used. Specifically, pulp fibers (L/N mixed pulp) were used which contained leaf bleached kraft pulp (LBKP, manufactured by Nippon Paper Industries, Co. Ltd.) and needle bleached kraft pulp (NBKP, manufactured by Nippon Paper Industries, Co. Ltd.) with a weight ratio of 8:2 and in which a Canadian standard freeness was adjusted to 400 ml with use of a single disk refiner (SDR).

Figure 1:
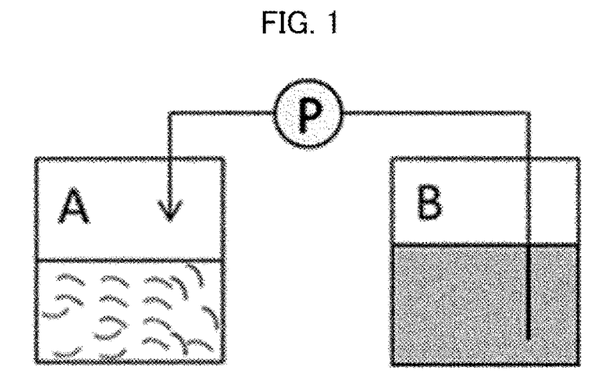
FIG. 1 is a schematic view illustrating a structure of a device which is used in Examples for synthesizing composite fibers.
Figure 2:
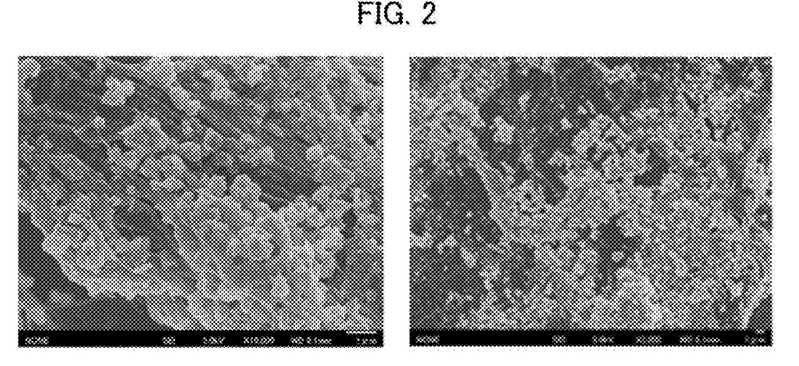
FIG. 2 is a view showing results of electron microscope observation of the composite fibers produced in Examples 1 and 2 (left: 10000 times, right: 3000 times).

The pulp fibers were added to the alkaline solution, and thus an aqueous suspension containing pulp fibers (pulp fiber concentration: 2.03%, pH: approximately 12.4) was prepared. The aqueous suspension (having a pulp solid content of 90 g) was put in a 10 L reactor vessel, and the acid solution (Zn-base) was dripped while the aqueous suspension was stirred, and thus hydrotalcite fine particles and fibers were synthesized into composite fibers ($Zn_6Al_2(OH)_{16}CO_3.4H_2O$). The device as illustrated in FIG. 1 was used, a reaction temperature was 60° C., and a drip rate was 15 ml/min, and the dripping was stopped when the pH of the reaction liquid reached approximately pH 7.0. After the dripping was finished, the reaction liquid was stirred for 30 minutes and washed with 10 times as much water to remove salts. Moreover, with use of an electron microscope, a surface of composite fiber in the slurry of the obtained composite fibers was observed (FIG. 2). In FIG. 2, a left image is a result observed with a magnification of 10000 times, and a right image is a result observed with a magnification of 3000 times. As a result of the observation, it was found that the fiber surface was covered by 15% or more, and the average primary particle diameter was 1 µm or less.

(1-3) Evaluation of Composite Fibers

Based on JIS P 8222, a mat was produced from the synthesized composite fibers (basis weight: approximately 100 g/m²). Specifically, aqueous slurry of composite fibers (approximately 0.5%) was filtered with use of a filter paper (JIS P3801, for quantitative analysis, No. 5B), and a sample thus obtained was dehydrated under pressure at 1 MPa for 5 minutes, and then the sample was dried with tension for 2 hours at 50° C. Thus, a mat of composite fibers having a size of approximately 200 cm² was produced. The mat was produced by using the composite fibers (referred to as "Zn-base HT composite" in Table 1) in combination with L/N mixed pulp and an absorbent article carrying metal ions (i.e., copper ions) (pamphlet of International Publication No. 2016/31749) (referred to as "metal ion-carrying pulp" in Table 1). Compositions of respective mats are indicated in Table 1.

(1-4) Evaluation of Deodorizing Characteristic

With use of the produced composite fiber mat (basis weight: approximately 100 g/m²), a deodorizing characteristic of the composite fibers was evaluated. A size of the composite fiber mat subjected to the deodorizing test was 100 cm² (10 cm×10 cm).

The deodorizing test was carried out based on a method of the certification standards of SEK mark textile products (JEC301, Japan Textile Evaluation Technology Council), and deodorizing characteristics with respect to ammonia, isovaleric acid, hydrogen sulfide, methyl mercaptan, nonenal, trimethylamine, and pyridine, were evaluated. Quantitative determinations of ammonia, hydrogen sulfide, methyl mercaptan, pyridine, and trimethylamine were carried out with use of a detecting tube, and quantitative determinations of isovaleric acid and nonenal were carried out by gas chromatography.

The samples were subjected to humidity control at 20° C. and 65% RH for 24 hours or more, and then deodorizing characteristics (rate of decrease, %) with respect to odor components were evaluated. Here, the rate of decrease (%) can be obtained by the following formula based on an initial concentration and a measured concentration of the odor component.

Rate of decrease (%)={$(A-B)/A$}×100

A: Blank test concentration after 2 hours
B: Sample test concentration after 2 hours As shown in Table 1, it was confirmed that the deodorizing property was improved by using the composite fibers in combination with the metal ion-carrying pulp among the samples subjected to the deodorizing test.

TABLE 1

| | | Ex. 1 | Ex. 2 | Com. Ex. 1 | Com. Ex. 2 | Com. Ex. 3 |
|---|---|---|---|---|---|---|
| Basis Weight (g/m$^2$) | | 110 | 109 | 109 | 108 | 111 |
| Mixed Ratio (% by mass) | L/N mixed pulp | 46.5 | 74.4 | 50 | 80 | 100 |
| | Metal ion-carrying pulp | 3.5 | 5.6 | 0 | 0 | 0 |
| | Zn-base HT composite | 50 | 20 | 50 | 20 | 0 |
| Rate of Decrease (%) | Ammonia | 97 | 98 | 92 | 83 | 84 |
| | Isovaleric acid | 99 | ≥99 | ≥99 | ≥99 | 99 |
| | Hydrogen sulfide | 100 | 100 | 100 | 100 | 10 |
| | Methyl mercaptan | 99 | 99 | 96 | 88 | 15 |
| | Trimethylamine | 73 | 50 | 64 | 29 | 30 |
| | Pyridine | 99 | 83 | 92 | 74 | 26 |
| | Nonenal | 94 | 88 | 94 | 85 | 33 |

Example 3: Composition of Hydrotalcite Composite Fiber Sheet and Titanium Oxide (1) Preparation of Alkaline Solution and Acid Solution A solution for synthesizing hydrotalcite (HT) was prepared. As an alkaline solution (solution A), a mixed aqueous solution was prepared which contained $Na_2CO_3$ (Wako Pure Chemical Industries, Ltd.) and NaOH (Wako Pure Chemical Industries, Ltd.) As an acid solution (solution B), a mixed aqueous solution was prepared which contained $MgSO_4$ (Wako Pure Chemical Industries, Ltd.) and $Al_2(SO_4)_3$ (Wako Pure Chemical Industries, Ltd.)

Alkaline solution (solution A, $Na_2CO_3$ concentration: 0.05 M, NaOH concentration: 0.8 M)

Acid solution (solution B, $MgSO_4$ concentration: 0.3 M, $Al_2(SO_4)_3$ concentration: 0.1 M)

(2) Synthesis of Composite Fibers

As fibers to be complexed, cellulosic fibers were used. Specifically, pulp fibers were used which contained leaf bleached kraft pulp (LBKP, manufactured by Nippon Paper Industries, Co. Ltd.) and needle bleached kraft pulp (NBKP, manufactured by Nippon Paper Industries, Co. Ltd.) with a mass ratio of 8:2 and in which a Canadian standard freeness was adjusted to 430 ml with use of a single disk refiner (SDR).

(3) Preparation of Composition

The pulp fibers were added to the alkaline solution, and thus an aqueous suspension (slurry) containing pulp fibers (pulp fiber concentration: 2.0%, pH: approximately 12.7) was prepared. The aqueous suspension (having a pulp solid content of 18.75 g) was put in a 2 L reactor vessel and sufficiently stirred.

While stirring the aqueous suspension, the acid solution was dripped. Note that a reaction temperature was 50° C., and a drip rate was 6 ml/min, and the dripping was stopped when the pH of the reaction liquid reached approximately 8. Thus, composite fibers of hydrotalcite ($Mg_6Al_2(OH)_{16}CO_3 \cdot 4H_2O$) and pulp fibers were synthesized. Further, after the dripping was finished, 20 parts to 50 parts of titanium oxide (R-3L, manufactured by Sakai Chemical Industry Co., Ltd.) was added to the composite fibers, and the reaction liquid was stirred for 30 minutes. After that, salt was removed by cleaning with use of 10 times as much water, and a composition including titanium oxide fine particles, hydrotalcite ($Mg_6Al_2(OH)_{16}CO_3 \cdot 4H_2O$), and pulp fibers was obtained. As a result of observing a surface of the obtained composition by SEM/EDS, the titanium oxide and magnesium and aluminum constituting the hydrotalcite were detected, and it was confirmed that those substances exist uniformly on the surface.

(4) Evaluation of Composition

Based on JIS P 8222, a mat was produced from the synthesized composite fibers (basis weight: approximately 100 g/m$^2$). Specifically, aqueous slurry of composite fibers (approximately 0.5%) was filtered with use of a filter paper (JIS P3801, for quantitative analysis, No. 5B), and a sample thus obtained was dehydrated under pressure at 1 MPa for 5 minutes, and then the sample was dried with tension for 2 hours at 50° C. Thus, a mat of composite fibers having a size of approximately 200 cm$^2$ was produced (referred to as "titanium oxide-HT composite fibers" in Table 2). In addition, a mat of only pulp (L/N mixed pulp, 8:2) was produced.

With use of the produced composite fiber mat (basis weight: approximately 100 g/m$^2$), a deodorizing characteristic of the composite fibers was evaluated. A size of the composite fiber mat subjected to the deodorizing test was 100 cm$^2$ (10 cm×10 cm). The deodorizing test was carried out based on a method of the certification standards of SEK mark textile products (JEC301, Japan Textile Evaluation Technology Council), a deodorizing characteristic with respect to ammonia was evaluated, and quantitative determination was carried out with use of a detecting tube. The samples were subjected to humidity control at 20° C. and 65% RH for 24 hours or more, and then deodorizing characteristics (rate of decrease, %) with respect to odor components were evaluated. Here, the rate of decrease (%) can be obtained by the following formula based on an initial concentration and a measured concentration of the odor component.

Rate of decrease (%)={$(A-B)/A$}×100

A: Blank test concentration after 2 hours
B: Sample test concentration after 2 hours As shown in Table 2, it was confirmed that the deodorizing property was improved by using the composite fibers in combination with the titanium oxide.

Further, as a result of measuring opacity (JIS P 8149: 2000), as shown in Table 2, it was confirmed that the opacity was improved by using the composite fibers in combination with the titanium oxide.

TABLE 2

| | Titanium oxide-HT composite fibers | Pulp only |
|---|---|---|
| Ammonia (%) | 99 | 84 |
| Opacity (%) | 97 | 89 |

Example 4: Composition Containing Hydrotalcite Composite Fibers and Magnesium Carbonate Composite Fibers (1) Synthesis of Composite Fibers Composed of Hydrotalcite and Cellulosic Fibers The composite fibers were synthesized by carrying out processes identical with those in Example 1.

(2) Synthesis of Composite Fibers Composed of Magnesium Carbonate and Cellulosic Fibers As fibers to be complexed, cellulosic fibers were used. Specifically, pulp fibers were used which contained leaf bleached kraft pulp (LBKP, manufactured by Nippon Paper Industries, Co. Ltd.) and needle bleached kraft pulp (NBKP, manufactured by Nippon Paper Industries, Co. Ltd.) with a mass ratio of 8:2 and in which a Canadian standard freeness was adjusted to 430 ml with use of a single disk refiner (SDR).

Figure 3:
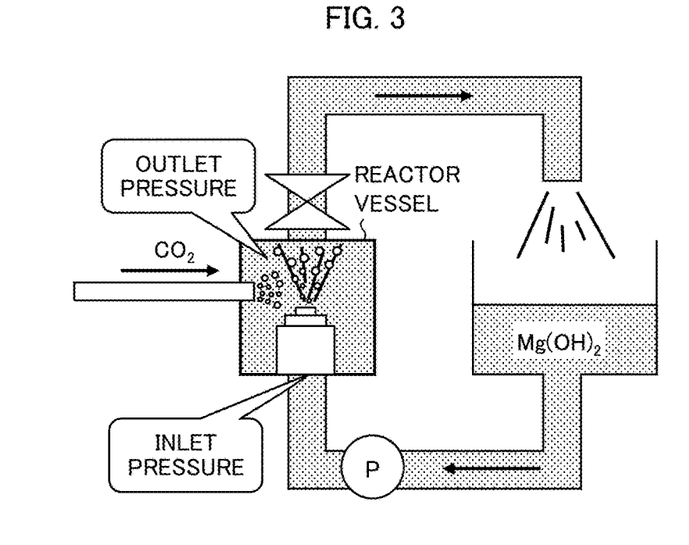
FIG. 3 is a schematic view illustrating a structure of a device which is used in Example 4 for synthesizing composite fibers.

0.8 kg of magnesium hydroxide (Ube Material Industries, Ltd., UD653) and 0.8 kg of the pulp fibers were added to water, and thus an aqueous suspension (40 L) was prepared. As illustrated in FIG. 3, the aqueous suspension was put in a cavitation device (50 L capacity), and composite fibers of magnesium carbonate fine particles and fibers were synthesized by a carbon dioxide process by blowing carbonic acid gas into a reactor vessel while circulating a reaction solution. A reaction start temperature was approximately 40° C., the carbonic acid gas was supplied from a commercially available liquefied gas, and a blowing rate of the carbonic acid gas was 2 L/min. When pH of the reaction liquid became approximately 7.5, introduction of $CO_2$ was stopped (pH before reaction was 10.2), followed by generation of cavitation and circulation of slurry in the device for 30 minutes to obtain slurry of composite fibers.

In synthesizing the composite fibers, cavitation bubbles were generated in the reactor vessel by circulating the reaction solution and injecting the reaction solution into the reactor vessel as shown in FIG. 3. Specifically, cavitation bubbles were generated by injecting the reaction solution at a high pressure through a nozzle (nozzle diameter: 1.5 mm), and a jet velocity was approximately 70 m/s, inlet pressure (upstream pressure) was 7 MPa, and outlet pressure (downstream pressure) was 0.3 MPa.

(3) Preparation of Composition Containing Composite Fibers Composed of Hydrotalcite and Cellulosic Fibers and Composite Fibers Composed of Magnesium Carbonate and Cellulosic Fibers A composition 1 containing composite fibers composed of hydrotalcite and cellulosic fibers and composite fibers composed of magnesium carbonate and cellulosic fibers was prepared by adding 100 ppm (with respect to solid content) of a cationic retention aid (ND300, HYMO Co., Ltd) and 100 ppm (with respect to solid content) of an anionic retention aid (FA230, HYMO Co., Ltd) to slurry of the composite fibers composed of hydrotalcite and cellulosic fibers (concentration: 1.2% by weight) and to slurry of the composite fibers composed of magnesium carbonate and cellulosic fibers (concentration: 1.2% by weight).

(4) Evaluation of Composition (4-1) Evaluation of Deodorizing Property

Based on JIS P 8222, a mat was produced from the synthesized composite fibers (basis weight: approximately 100 g/m$^2$). Specifically, aqueous slurry of the composition 1 (i.e., the composition containing the hydrotalcite composite fibers and the composite fibers composed of magnesium carbonate and cellulosic fibers) (approximately 0.5%) was filtered with use of a filter paper (JIS P3801, for quantitative analysis, No. 5B), and a sample thus obtained was dehydrated under pressure at 1 MPa for 5 minutes, and then the sample was dried with tension for 2 hours at 50° C. Thus, a mat of composite fibers having a size of approximately 200 cm$^2$ was produced (referred to as "Mg carbonate composite fiber-HT composite fibers" in Table 3). In addition, a mat of only pulp (L/N mixed pulp, 8:2) was produced.

With use of the produced composite fiber mat (basis weight: approximately 100 g/m$^2$), a deodorizing characteristic of the composite fibers was evaluated. A size of the composite fiber mat subjected to the deodorizing test was 100 cm$^2$ (10 cm×10 cm). The deodorizing test was carried out based on a method of the certification standards of SEK mark textile products (JEC301, Japan Textile Evaluation Technology Council), a deodorizing characteristic with respect to ammonia was evaluated, and quantitative determination was carried out with use of a detecting tube. The samples were subjected to humidity control at 20° C. and 65% RH for 24 hours or more, and then deodorizing characteristics (rate of decrease, %) with respect to odor components were evaluated. Here, the rate of decrease (%) can be obtained by the following formula based on an initial concentration and a measured concentration of the odor component.

Rate of decrease (%)={(A−B)/A}×100

A: Blank test concentration after 2 hours
B: Sample test concentration after 2 hours As shown in Table 3, it was confirmed that the deodorizing property was improved by using the composite fibers composed of hydrotalcite and cellulosic fibers in combination with the composite fibers composed of magnesium carbonate and cellulosic fibers.

(4-2) Evaluation of Flame Retardant Characteristic

Based on JIS P 8222, a mat was produced from the Mg carbonate-HT composite fibers (basis weight: approximately 300 g/m$^2$). A flame retardant characteristic of the produced mat was evaluated. The evaluation was carried out in accordance with the following procedures based on JIS A 1322 (JIS Z 2150). A board cut into a certain size (20 cm×30 cm) was dried at 50° C. for 48 hours, and was left in a desiccator for 24 hours with a silica gel for drying, and thus a sample for a combustion test (heating test) was obtained. The sample was attached to a supporting frame (inside dimensions of frame: 16 cm×25 cm) and the supporting frame with the sample was mounted on a heating test device. The sample was heated for 2 minutes after ignition of a gas burner, and a carbonized area, an afterflame time, and an afterglow time were measured. Note that, in the combustion test, a 45° flammability test instrument (manufactured by Suga Test Instruments Co., Ltd., FL-45M) was used. In the heating, a Meker burner (height: 160 mm, inner diameter: 20 mm) was used, and the combustion was carried out by supplying only the gas without mixing primary air. As a fuel, a liquefied petroleum gas No. 5 (mainly constituted by butane and butylene, JIS K 2240) was used, and flame was adjusted to have a length of 65 mm in a state in which the sample was not mounted.

Afterflame time: A time was measured during which the sample was burning with flame after the heating was finished.

Afterglow: A state of burning without flame after the heating was finished.

Carbonized length area: A maximum length and a maximum width of a carbonized part (i.e., a part whose strength was evidently changed by carbonization) in a heated surface of the sample were measured, and calculation was carried out by multiplying the maximum length and the maximum width together. As a result, a sample whose afterflame time was 10 seconds or less, afterglow time was 30 seconds or less, and carbonized area was 50 cm$^2$ or less was considered as satisfying the standard demanded for a fireproof article (plywood) (Reference: the Fire and Disaster Management Agency, "BOUEN NO CHISHIKI TO JISSAI (*Knowledge and Reality of Fire Prevention*)"), and was evaluated as "good". Moreover, a sample that did not meet the standard demanded for a fireproof article was evaluated as "bad". Table 3 shows the results. As shown in Table 3, the mat of this Example showed an excellent flame retardant characteristic.

TABLE 3

|  | Mg carbonate composite fiber-HT composite fibers | Pulp only |
| --- | --- | --- |
| Ammonia (%) | 91 | 84 |
| Flame retardancy | good | bad |

INDUSTRIAL APPLICABILITY

An aspect of the present invention is suitably applicable to the field of using fibers such as paper.

The invention claimed is:

1. A composition comprising:
   composite fibers comprising inorganic particles and fibers; and
   at least one of (i) other inorganic particles which are different from the inorganic particles, (ii) other fibers which are different from the fibers, and (iii) organic particles,
   wherein in the composite fibers, 15% or more of a surface of each of the fibers is covered with the inorganic particles, and
   wherein the fibers and the inorganic particles are bonded together.

2. The composition as set forth in claim 1, wherein the other fibers are metal-carrying fibers.

3. The composition as set forth in claim 2, wherein a metal, which fibers carry in the metal-carrying fibers, includes a compound that contains at least one metal selected from the group consisting of gold, silver, titanium, copper, platinum, iron, zinc, and aluminum.

4. The composition as set forth in claim 1, wherein the other fibers are composite fibers comprising inorganic particles and fibers.

5. The composition as set forth in claim 1, wherein
   the other inorganic particles include a compound containing at least one metal selected from the group consisting of gold, silver, titanium, copper, platinum, iron, zinc, and aluminum.

6. The composition as set forth in claim 1, wherein
   the other inorganic particles include at least one compound selected from the group consisting of titanium oxide, calcium carbonate, magnesium carbonate, and aluminum hydroxide.

7. The composition as set forth in claim 1, wherein the first fibers in the composite fibers are cellulosic fibers.

8. The composition as set forth in claim 1, wherein an average primary particle diameter of the inorganic particles in the composite fibers is 1 μm or less.

9. A composition comprising:
   composite fibers comprising inorganic particles and fibers; and
   at least one of (i) other inorganic particles which are different from the inorganic particles, (ii) other fibers which are different from the fibers, and (iii) organic particles,
   the inorganic particles in the composite fibers being hydrotalcite.

10. The composition as set forth in claim 9, wherein ash of the composite fibers comprising hydrotalcite and the fibers contains at least one of magnesium and zinc in an amount of not less than 10% by weight.

* * * * *